United States Patent [19]

Essex et al.

[11] Patent Number: 5,045,448

[45] Date of Patent: Sep. 3, 1991

[54] METHOD AND PRODUCTS FOR DETECTION OF HUMAN T CELL LEUKEMIA VIRUS

[75] Inventors: Myron E. Essex, Sharon; Tun-Hou Lee, Newton, both of Mass.

[73] Assignee: President and Fellows of Harvard College, Cambridge, Mass.

[21] Appl. No.: 131,201

[22] Filed: Dec. 10, 1987

Related U.S. Application Data

[63] Continuation of Ser. No. 598,673, Apr. 13, 1984, Pat. No. 4,743,678, which is a continuation-in-part of Ser. No. 489,187, Apr. 27, 1983, abandoned.

[51] Int. Cl.⁵ .................. G01N 33/569; G01N 33/535
[52] U.S. Cl. ..................................... 435/5; 435/7.92; 435/975; 435/235.1; 530/350; 530/395
[58] Field of Search ............... 435/5, 235, 7.92, 235.1, 435/975; 530/350, 395

[56] References Cited

U.S. PATENT DOCUMENTS

| | | |
|---|---|---|
| 4,126,671 | 11/1978 | House et al. |
| 4,282,315 | 8/1981 | Luderer et al. |
| 4,379,839 | 4/1983 | Spiegelman |
| 4,689,398 | 8/1987 | Wu et al. ............................. 530/327 |

OTHER PUBLICATIONS

Yoshida et al., "Isolation and Characterization of Retrovirus from Cell Lines of Human Adult T-cell Leukemia and Its Implication in the Disease", Proc. Natl. Acad. Sci. USA, 79, (1982), 2031-5.
Potocnjak et al., Science, 215, (1982), 1637-1639.
Essex et al., J. Natl. Cancer Inst., 69, (1982), 981-5.
Kalyanaraman et al., J. Virol., 38(2), 1981:906-15.
Poiesz et al., Proc. Natl. Acad. Sci. USA, 77, (1980), 7415-19.
Koyanagi et al., "Expression of HTLV-Specific Polypeptides in Various Human T-cell Lines", Med. Microbiol. Immunol, 173, (1984), 127-140.
Taguchi et al., GANN, 74, (1983), 185-187.
Samuel, "Diagnostic Potential for Human Malignancies of Bacterially Produced HTLV-I Envelope Protein", Science, 226, (1984), 1094-7.
Hattori et al., "Identification of Gag and Env Gene Products of Human T-cell Leukemia Virus (HTLV)", Virol., 136, (1984), 338-47.
Kiyokawa et al., "Envelope Proteins of Human T-cell Leukemia Virus: Expression in *Escherichia coli* and Its Application to Studies Env Gene Functions", Proc. Natl. Acad. Sci. USA, 81, (1984), 6202-6.
Schüpbach et al., "Antigens on HTLV-Infected Cells Recognized by Leukemia and AIDS Sera are Related to HTLV Viral Glycoprotein", Science, (1984), 607-610.
Essex et al., "Antibodies to Human T-cell Leukemia Virus Membrane Antigens (HTLV-MA) in Hemophiliacs", Science, 221, (1983), 1061-1064.
Yamamoto et al., "Adult T-cell Leukemia (ATL) Virus-Specific Antibodies in ATL Patients and Healthy Virus Carriers", Int. J. Cancer, 32, (1983), 281-287.
Essex et al., "Antibodies to Cell Membrane Antigens Associated with Human T-cell Leukemia Virus in Patients with AIDS", Science, 220, (1983), 859-62.
Yamamoto et al., "Adult T-cell Leukemia-Associated Antigen (ATLA): Detection of a Glycoprotein in Cell- and Virus-Free Supernatant", Z. Naturforsch, 37c, (1982), 731-2.
Seiki et al., "Human Adult T-cell Leukemia Virus: Complete Nucleotide Sequence of the Provirus Genome Integrated in Leukemia Cell DNA", Proc. Natl. Acad. Sci. USA, 80, (1983), 3618-22.
Sugamura et al., "Identification of a Glycoprotein, gp21 of Adult T-cell Leukemia Virus by Monoclonal Antibody", J. Immunol., 132, (1984), 3180-4.
Devare, S. G. et al., Journal of Virology, 23(2):443-447, (1977).
Hopp et al., Proc. Natl. Acad. Sci., 78(6):3824-3828, (1981).
Prince et al., Proc. Natl. Acad. Sci., 9:579-582, (1982).
Fine et al., Virology, 101:176-184, (1980).
Azocar et al., JNCI, 63:1179-1184, (1979).
Hinuma et al., PNAS USA, 78:6476-6480, (1981).
Posner et al., J. Exp. Med. 154:333-344, (1981).
Robert-Guroff et al., Science, 215:975-978, (1982).
Fields et al., Nature, 300:19-23, (1982).
Hinuma, GANN Monograph on Cancer Research, 28:211-218, (1982).
Miyoshi et al., GANN Monograph on Cancer Research, 28:219-237, (1982).
Popovic et al., Science, 219:856-859, (1983).
Miyoshi et al., GANN Monograph etc., 74:1-4, (Feb. 1983).
Sacks et al., J. Exp. Med., 155:1108-1119, (1982).
Poiesz et al., Nature, 294:268-271, (1981).
Robert-Guroff et al., Journal of Experimental Medicine, 154:1957-1964, (1981).
Kalyanaraman et al., Science, 218:571-573, (1982).
Robert-Guroff et al., Virology, 122:297-305, (1982).
Kalyanaraman et al., Nature, 294:271-273, (1981).
Oroszlan et al., Proc. Natl. Acad. Sci., 79:1291-1294, (1982).
Kalyanaraman et al., Proc. Natl. Acad. Sci., 79:1653-1657, (1982).
Gallo et al., Science, 220:865-867, (1983).
Barre-Sinoussi, Science, 220:868-871, (1983).
Marx et al., Science, 223:1083-1086, (1984).
Palker et al., Journal of Experimental Medicine, 159:1117-1131, (1984).

*Primary Examiner*—Christine Nucker

[57] ABSTRACT

A first glycoprotein having a molecular weight of approximately 61,000-68,000 daltons in the MJ, C5-MJ, C91 PL or HUT-102 cell lines, of which 46,000 to 48,000 is the unglycosylated moiety, is obtained from cells infected with human T cell leukemia virus. A second glycoprotein having a molecular weight of approximately 45,000-52.000 daltons is also obtained from such cells and is in large part identical to the $NH_2$-terminal end of the first glycoprotein. The presence, in a biological specimen, of antibody to the antigenic determinant of either of these proteins is indicative of the presence of cells infected by human T cell leukemia virus. An assay for the antibody is a useful diagnostic procedure for determining such infection in biological specimens.

16 Claims, No Drawings

METHOD AND PRODUCTS FOR DETECTION OF HUMAN T CELL LEUKEMIA VIRUS

This invention was made in the course of work supported by the United States Government, which has certain rights in the invention.

This application is a continuation of application Ser. No. 598,673, filed Apr. 13, 1984, now U.S. Pat. No. 4,743,678, which is a continuation-in-part of our copending application Ser. No. 489,187 filed Apr. 27, 1983.

This invention relates to a novel purified forms of glycoprotein found in the cell surface membrane of cells infected with human T cell leukemia virus, and to an assay for detecting in a biological specimen the presence of an antibody to the antigenic determinants present in said glycoproteins.

The human T cell leukemia virus (HTLV) is known to be closely associated with a particular type of human leukemia, the T cell type in adults. It has also been shown that all people whose bodies contain antibodies to this virus are apparently latently infected with the virus. Essex, Journal of the National Cancer Institute, Vol. 69, 981–5 (1982). The major core proteins of the virus have been studied and an immunofluorescent assay procedure for antibodies to the infected cells has been described which involves fixing cells from a cell line of infected human cells such as MT1 or MT2, contacting the fixed cells with the test serum to be assayed, and determining whether bonding of the serum to the cell surface has occurred by subsequently contacting with a fluorescent-labelled antibody to human IgG. Hinuma et al., Proc.Natl.Acad.Sci., Vol. 78, 6476–6480 (1981). This assay is tedious and difficult to use because only 1 to 5% of the fixed cells display the necessary antigenic characteristics. It has also been proposed to employ a somewhat analogous cell surface immunofluorescent assay in which a culture of infected cells is incubated with test serum, then with fluorescent-labelled rabbit antibody to human IgG to determine whether bonding of serum to cells has occurred. Robert-Guroff et al., Science, Vol. 215, 975–978 (1982). A radioimmunoassay for antibodies to p24 and p19, two of the core proteins of HTLV, has also been described. Posner et al., J.Exp.Med., Vol. 154, 333–344 (1981). However, this assay fails to produce positive results for all individuals who have been exposed to the infecting virus and are therefore at risk, but who do not have detectable levels of antibodies to these two antigens.

SUMMARY OF THE INVENTION

It has now been found that particular polypeptides or glycoproteins present on the cell surface of human T cells infected with HTLV when purified and isolated contain an antigenic determinant or determinants which provide a high degree of sensitivity and immunospecificity for antibody to human cells infected with HTLV, to human T cell leukemia cells, and/or to HTLV. Consequently, the substantially pure glycoproteins or their unglycosylated moieties are useful as a diagnostic tool for assaying biological specimens to determine whether they contain cells which have been infected by HTLV. Other polypeptides containing immunologically cross-reactive antigenic determinants are useful for the same purpose. By "polypeptides containing immunologically cross-reactive antigenic determinants" is meant polypeptides having in common antigenic determinants with which a given antibody will react. Such other polypeptides include the unglycosylated moieties of the glycoproteins. Other useful polypeptides or proteins, which have the necessary immunogenic determinants, include synthetic polypeptides. They also include antibodies or fragments thereof which are anti-idiotypic towards the active determinant or determinants on the glycoprotein of the invention. It has recently been shown that anti-idiotypic monoclonal antibodies can induce an immune response against, and protect against infection by infectious organisms carrying antigenic determinants which are the same or substantially the same as those on the anti-idiotypic antibodies (Fields el al., Nature, 300:19–23 (1982) Sacks et al., J.Exp.Med. Vol. 155, 1108–1119 (1982)). It has also been shown that anti-idiotypic reagents are useful as diagnostic tools for the detection of antigens carrying sites which are immunologically cross-reactive with those on the antibodies (Potocnjak et al., Science 215: 1637–1639 (1982). Thus, an assay for HTLV could be carried out with the aid of a anti-idiotypic antibody or immunologically active fragment thereof which carries an antigenic site or sites thereon which are immunologically similar to the antigenic site or sites on the glycoprotein of the invention. Such anti-idiotypic antibodies can be raised against first antibodies having specificity against the antigenic sites on the glycoprotein of the invention (i.e. the anti-idiotypic antibodies are antiantibodies). Preferably monoclonal anti-idiotypic antibodies are used.

An assay for HTLV infection is important because the virus can be readily transferred from the peripheral blood leukocytes of antibody-positive people to leukocytes of antibody-negative people when the two are cultivated together. Popovic et al., Science, Vol. 219, 856–859 (1983). Consequently, it appears that there is great risk of infection involved in whole blood transfusions when the transfused blood contains infected cells. In addition, the assay is of importance because biological specimens from individuals exhibiting acquired immunodeficiency syndrome (AIDS) also give a positive test for antibodies to the antigenic determinant of the novel glycoprotein, thus facilitating diagnosis of that disease.

Consequently, the invention also embraces the method of assaying a biological specimen for the presence of antibody to HTLV-infected cells which comprises incubating said specimen with a polypeptide having an antigenic determinant or determinants immunologically cross-reactive with those of a glycoprotein having a molecular weight of approximately 61,000–68,000 daltons, of which approximately 46–48,000 daltons is the unglycosylated moiety, or with a glycoprotein having a molecular weight of approximately 45,000 to 52,000 daltons, which glycoproteins occur on the cell surface of cells infected with HTLV, and determining whether or not an immunocomplex is formed between said antibody and said polypeptide.

The invention also embraces a method of assaying a biological specimen for the presence of antigenic determinant or determinants immunologically cross-reactive with the determinants of the glycoproteins of molecular weight 61,000–68,000 daltons, or 45,000–52,000 daltons. The determinants to be assayed may occur on the stated glycoproteins themselves or on other polypeptides. They may be in free circulation in the body fluids or in lymphocytes. The assay can be carried out by known immunoassay methods, using antibodies, monoclonal or polyvalent, having immune reactivity with the antigenic determinants found on the stated glycoproteins. For example competitive immunoassays or immunometric (sandwich) assays can be used.

The glycoproteins of the present invention have a molecular weight of approximately 61,000–68,000 daltons and approximately 45,000–52,000 daltons as determined by sodium dodecyl sulfate (SDS) gel electrophoresis and are soluble in SDS buffer consisting of 0.15M sodium chloride, 0.05M Tris hydrochloride pH 7.2, 1% Triton X-100, 1% sodium deoxycholate, 0.1% sodium dodecylsulfate, and 1 nM phenylmethylsulfonyl fluoride. Triton X-100 is a nonionic detergent (octylphenoxy polyethoxy (9-10) ethanol). The unglycosylated moiety of the 61,000–68,000 d glycoprotein has a molecular weight of approximately 46,000–48,000 daltons and contains substantially the same antigenic determinant or determinants as does the glycoprotein itself.

The glycoproteins can be obtained from HTLV-infected cells. A variety of cell lines have been prepared, which are permanently and persistently infected with HTLV; among them can be mentioned MJ, C5-MJ, C91PL, and HUT-102. It may be that the exact sizes of the novel glycoproteins are slightly different in different lines; however, the common immunologically cross-reactive portion of the glycoproteins is the same regardless of cell line, since it is a protein induced by HTLV. Thus, any cell which harbors the virus may be an appropriate source for the novel glycoproteins In order to obtain the protein from any infected cells carrying the virus, the cells are metabolically labelled (e.g. with $^{35}$S-methionine) and immunoprecipitated with antisera obtained from HTLV infected subjects. The novel glycoproteins can then be detected and isolated by gel electrophoresis By "HTLV" as used in the present specification and claims it is meant to include the virus generically. Thus any and all forms, subtypes, or variations of the virus are included.

For example, the glycoproteins are present at the cell surfaces of the human T cell leukemia cell cultures MJ, C5-MJ, C91PL and HUT-102. A specimen of MJ and of C5-MJ, have been deposited with the American Type Culture Collection (Rockville, Md.) on Apr. 26, 1983 as CRL-8294 and CRL-8293, respectively. The glycoproteins can readily be separated from the cells of these cell lines by lysis thereof and SDS gel electrophoresis.

The purified and isolated glycoproteins or any antigen immunologically cross-reactive therewith can be employed as a standard antigen in any conventional assay procedure for detection in biological specimens of the presence of antibodies specific thereto, hence of the presence in the specimen of cells infected with HTLV and/or symptomatic of AIDS. The antibodies specific to such HTLV antigens are not found in patients suffering from diseases such as hepatitis which are not accompanied by HTLV infection.

The glycoproteins or polypeptides immunologically cross-reactive therewith can be labelled by conventional procedures with $^{125}$I or $^{35}$S or $^{3}$H for use in radioimmunoassay, with fluorescein for fluorescent immunoassay, with enzyme for enzyme immunoassay or with biotin, for biotin-avidin linked assays. It can be employed, labelled or unlabelled as desired, in competitive immunoassays, as well as in double antibody assays using two antibodies, either of the idiotype:anti-idiotype variety or more particularly of the second antibody type using an anti-Fc antibody, or other assays.

Alternatively, the novel glycoproteins or polypeptides immunologically cross-reactive therewith could be immobilized on an insoluble phase, such as an insoluble resin, and detection of the anti-glycoprotein antibodies is carried out by measuring their binding to the insoluble phase. Insoluble phases also include latex particles, which, when coated with the novel glycoprotein or its immunologically cross-reactive polypeptides and subjected to anti-glycoprotein antibody, will agglutinate. Yet other insoluble phases include test tubes, vials, titration wells, and the like, to which the novel glycoprotein or its immunologically cross-reactive polypeptide can be bound, and antibody thereto detected by double antibody techniques or Protein-A dependent techniques.

The assay for antibody to HTLV may utilize the glycoprotein or glycoproteins of m.w. 61–68,000 and 46–52,000, respectively, in crude form, and is not limited to using these proteins in substantially pure form. For example, the glycoprotein(s) may be first substantially purified and then mixed together. Alternatively cruder mixtures can also be used. In one embodiment, the assay for the presence of antibodies against HTLV may include detection of additional antibodies in the specimen such as those against HTLV core proteins p19, p24 or a mixture of both of the latter. In this embodiment the method comprises incubating the specimen with a reagent comprising 1) one or both glycoproteins of the invention (i.e. 61,000–68,000 and/or 46,000–52,000 Kd or immunocross-reactive polypeptides) and, optionally, 2) HTLV core proteins p24 or p19 or both, and determining whether or not an immunocomplex is formed between antibodies in the specimen and the reagent.

The elements necessary for carrying out the diagnostic methodology described hereinbefore may be present in a kit. Such kit comprises a carrier being compartmentalized to receive therein one or more containers, each of said containers comprising one or more elements necessary to carry out the tests.

For example, the first container may contain one or both of the purified glycoproteins or its immunologically cross-reactive polypeptides in detectably labelled or in insolubilized form.

A second container may comprise anti IgG antibody, polyclonal or monoclonal, useful in double antibody binding assay, or elements needed for detection of the label on the glycoprotein or its immunologically cross-reactive polypeptides (e.g. chromogenic substrates).

Additional containers may comprise varying amounts of one of the glycoproteins or its immunologically cross-reactive polypeptides which can be used to prepare a standard curve into which experimental results can be interpolated. The materials may be present in the kit by themselves, in solution, freeze-dried, or in admixture with other inert materials, such as inert proteins, and the like.

The biological specimens tested may include blood, serum, lymphocytes, urine, tissues, saliva, feces, and the like. Of particular interest is the screening of blood in blood banks, to assure that the blood is not contaminated with HTLV. Screening of blood-derived products, such as vaccines, can also be done by the methods of the invention.

The following specific examples are intended to illustrate more fully the nature of the invention without acting as a limitation upon its scope.

EXAMPLE 1

Preparation of Labelled Glycoprotein

A. Human T cell leukemia cells from the two cell lines MJ and C5-MJ were separately harvested at their log phase of growth. After one wash with methionine-free McCoy's 5A medium, each sample of the cells was resuspended in a labelling medium consisting of methionine-free McCoy's 5A, 10% phosphate-buffered saline (PBS), dialyzed fetal bovine serum, and 100 μCi/ml of $^{35}$S-methionine. At the end of a 2 to 4 hour pulsing, the radioactive labelled cells were washed three times with cold PBS. The cell pellet was then lysed with 0.6 ml to 1.0 ml of cold lysis buffer (RIPA) (0.15M sodium chloride, 0.05M Tris-hydrochloride pH 7.2, 1% Triton X-100 wetting agent, 1% sodium deoxycholate, 0.1% sodium dodecyl sulfate, and 1 mM phenylmethylsulfonyl fluoride). After 10 minutes of intermittent vortexing, the mix was centrifuged for 1 hour at 100,000 xg at 4° C. The lysate supernatant was precleared of nonspecific binding components by absorption for one hour at 4° C. on carbohydrate beads (Sepharose CL-4B) coated with protein-A.

B. Labelling of cell surface membrane protein was carried out by lactoperoxidase catalyzed radioiodination. Three aliquots of $5 \times 10^6$ cells of each line with greater than 99% viability were iodinated separately with 1 mCi of carrier-free sodium $^{125}$iodide in the presence of 50 μl carrier-supported lactoperoxidase and glucosidase (Enzymobeads, Bio-Rad Labs.) and 25 μl of 1% beta-D-glucose. After the reaction was terminated, three aliquots of iodinated cells were pooled and subjected to the same lysing and preclearing procedures as described in (A) above.

C. MJ and C5-MJ cells at their peak log phase of growth were separately harvested, then resuspended in glucose-free RPMI-1640 medium supplemented with 1 mg/ml of sodium pyruvate for 2 hours. After this glucose starvation, the cells were labelled with 100 μCi/ml of $^3$H-glucosamine (New England Nuclear) for 5-6 hours. The procedure results in tritium labelling of only the glycoproteins present in the cells. The labelled cells were then subjected to lysing and preclearing procedures as described in (A) above.

PREPARATION OF LABELLED UNGLYCOSYLATED MOIETY OF GLYCOPROTEIN

D. MJ and C5-MJ cells at their peak log phase of growth were separately harvested and resuspended in McCoy's 5A medium supplemented with 10% fetal bovine serum, 1% of antibiotic-antimycotic mixture, and 20 μg/ml of tunicamycin for 2 hours. After this trimming step, the cells were labelled with 100 μCi/ml of $^{35}$S-methionine in the presence of 20 μg/ml of tunicamycin for 2 hours. The labelled material was then subjected to the same lysing and preclearing procedures as described in (A) above.

FORMATION OF PROTEIN-ANTIBODY COMPLEX

E. There were bound to aliquots of protein-A-coated beads (a) positive reference blood serum for individual known to harbor antibodies against cells infected with HTLV; (b) negative control serum from individuals free from infection; and (c) serum from unknown individuals to be tested. Each aliquot of coated beads was then reacted with an aliquot of each precleared lysate obtained from MJ and from C5-MJ from paragraph (A) above at 4° C. for 1-2 hours to permit complex formation or immunoprecipitation to occur between the bonded lysate protein and any antibody present in the sera. At the end of the reaction the beads were washed 4 times with the buffer (RIPA) and once with a buffer containing 0.05M Tris-hydrochloride pH 7.2 and 0.15M sodium chloride to remove uncomplexed lysate protein.

The beads were then immersed in a sample buffer (0.1M Cleland's reagent, 2% sodium dodecylsulfate, 0.08M Tris-hydrochloride pH 6.8, 10% glycerol, and 0.2% Bromphenol Blue) and subjected to boiling at 100° C. for 2 minutes to elute proteins from the beads and to dissociate complexes.

CHARACTERIZATION OF PROTEIN

F. Each sample from the foregoing procedure (A) was analyzed by electrophoresis, the proteins being separated on a 12.5% SDS-polyacrylamide gel with 3.5% stacking gel using the Laemmli buffer system. Molecular weight markers were run simultaneously in a parallel column. The markers used included $^{14}$C-labelled phosphorylase b (92,500), bovine serum albumin (68,000), and ovalbumin (46,000) carbonic anhydrase (30,000) and cytochrome C (12,000). For visualization by fluorography, the gels were first fixed with 10% acetic acid, 10% trichloroacetic acid, and 30% methanol for 1 hour, then immersed in Enhancer solution for 1 hour. After rinsing with distilled water and drying under vacuum, the gels were exposed on Kodak SB-5 film to provide autoradiographs.

The spots of purified and isolated 61,000–68,000 molecular weight glycoprotein and of 45,000–52,000 molecular weight glycoprotein appeared prominently in all of the columns of serum (a), but in none of those of serum (b). In contrast, the core proteins p19 and p24 failed to appear in all samples of serum (a). Appearance of the glycoprotein in the unknown sera (c) indicated the presence in the sera of cells infected with HTLV. Sera from individuals exhibiting AIDS also exhibited prominent evidence of antibodies to the 61,000–68,000 MW glycoprotein in this procedure.

Similar results have been obtained by substituting for the labelled glycoproteins of paragraph A, either of those of paragraphs B or C. There could also be substituted for it the labelled unglycosylated moiety of paragraph D, in which case the purified and isolated labelled moiety appears in the gel column at a location corresponding to molecular weight 46,000–48,000. Unlabelled glycoprotein and unlabelled unglycosylated moiety can be obtained by omitting the labelling steps in the foregoing procedures.

Similar results have been obtained by substituting cell lines C91PL or HUT-102 in place of MJ or C5MJ.

Amino Acid Sequence Analysis.

[$^{35}$S]cysteine-labeled glycoproteins having a molecular weight of approximately 61,000 daltons and of approximately 45,000–46,000 daltons, respectively, were precipitated from $36 \times 10^6$ Hut 102 cells metabolically labeled with 5 mCi of [$^{35}$S]cysteine (specific activity 1011.2 Ci/mmol, New England Nuclear) in 30 ml of cysteine-free RPMI-1640 media containing 15% fetal bovine serum (Grand Island Biological Co.) for 10 hours. The two glycoproteins were excised from NaDodSO$_4$ polyacrylamide gels and then individually subjected to electrophoretic elution in the presence of 50 mM Tris-acetate pH 7.8 buffer containing 0.01% NaDodSO$_4$ for 12-16 hours. Samples were dialyzed once with 10 mM of ammonium bicarbonate buffer containing 0.002% NaDodSO$_4$ for 12-16 hours. One more dialysis was done with 10 mM ammonium bicarbonate buffer without NaDodSO$_4$ for 12-16 hours. Each sample was then lyophilized and amino acid sequence analysis was conducted by the procedures described by Coligan et al., J. Immun. Meth., Vol. 47, 1-11 (1981) and Meth. Enzymol., Vol. 91, 413-434 (1983). Briefly, automated Edman degradation of radiolabeled peptides was performed utilizing a Beckman 890C sequencer with cold trap modification and 0.1M Quadrol program 121078. The butyl chloride extract from each sequence step was dried using N$_2$ evaporation in 7.0 ml scintillation vials. After addition of Biofluor (NEN), radioactivity was determined on a Beckman LS9080 liquid scintillation counter. [$^{35}$S] peaks were found at residues 6, 7, 21 and 28, indicating the presence of cysteine at these positions in the protein sequence of the 61,000-68,000 d glycoprotein. The repetitive yield for this sequence was 88%, indicating that all the residues are in the same sequence. Small peaks at positions 4 and 13 are presumably from small amounts (less than 5%) of contaminating proteins. These results indicate that the 61,000-68,000 mw glycoprotein is encoded, at least in part, by the env gene of HTLV and that the leader sequence of the env gene consists of 20 residues.

Similar analysis was carried out with [$^{35}$S] cysteine labeled glycoproteins having molecular weights of approximately 67,000 d and 50,000-52,000 d respectively. Cysteine residues were detected at positions 6, 7 and 21 when the first 22 NH$_2$-terminal residues were analyzed. This shows that this glycoprotein is also encoded, at least in part, by the same NH$_2$-terminal end of the env gene.

What is claimed is:

1. An essentially purified and essentially isolated antigen comprising human T-cell leukemia virus type I envelope glycoprotein having a molecular weight of approximately 61,000-68,000 daltons, or determinant-containing fragments of it or of its unglycosylated moiety, said envelope glycoprotein being characterized in that it is present in cells infected with human T-cell leukemia virus type I and its unglycosylated moiety is approximately 46,000-48,000 daltons.

2. The antigen of claim 1 wherein said antigen is present in human T-cell leukemia cell line ATCC No. CRL-8294 (MJ) or ATCC No. CRL-8293 (C5-MJ).

3. An antigen as claimed in claim 1 or 2 which is detectably labeled.

4. The antigen of claim 3 wherein said label is selected from the group consisting of a radiolabel, a fluorogenic label, an enzyme label, or a biotin label.

5. The antigen of claim 1 or 2 which is bound to an insoluble phase.

6. The polypeptide of claim 5 wherein said insoluble phase is a an insoluble resin.

7. A process for preparing the antigen of claim 1 comprising culturing a cell-line infected with HTLV-I under appropriate conditions and extracting said antigen from said cells.

8. The method of assaying a biological specimen for the presence of antibody indicative of invention with human T-cell leukemia virus, type I, which method comprises:
   incubating said specimen with an antigen according to claim 1, said incubating occurring for a time and under conditions sufficient to permit formation of immunocomplexes between said antigen and said antibody; and
   determining whether or not an immunocomplex is formed between said antibody and said antigen.

9. The method as claimed in claim 8 in which said antigen is said glycoprotein having a molecular weight of approximately 61,000-68,000 daltons.

10. The method as claimed in claim 8 in which said antigen is said unglycosylated moiety having a molecular weight of approximately 46,000-48,000 daltons.

11. The method as claimed in claim 8 which comprises including the step of providing said antigen in a detectably labeled form.

12. The method as claimed in claim 8 which is an enzyme linked immunoassay.

13. The method as claimed in claim 8 which is a radioimmunoassay.

14. The method as claimed in claim 8 which is a latex particle agglutination assay.

15. The method as claimed in claim 8 which is a fluorescence assay.

16. A kit useful for assaying a sample for the presence of human antibody to cells infected with human T-cell leukemia virus type I, said kit comprising the antigen of claim 1 in an amount sufficient for use in an immunoassay for antibody to said antigen.

* * * * *